(12) United States Patent
Piergallini et al.

(10) Patent No.: US 9,345,648 B2
(45) Date of Patent: *May 24, 2016

(54) PHOTOACTIVATABLE OXYGEN-EVOLVING COMPOSITIONS AND METHODS FOR TEETH WHITENING

(75) Inventors: Remigio Piergallini, Grottammare Ascoli Piceno (IT); Nikolaos Loupis, Athens (GR)

(73) Assignee: KLOX Technologies Inc., Laval (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/643,672

(22) PCT Filed: Apr. 29, 2011

(86) PCT No.: PCT/CA2011/050261
§ 371 (c)(1),
(2), (4) Date: Jan. 22, 2013

(87) PCT Pub. No.: WO2011/134087
PCT Pub. Date: Nov. 3, 2011

(65) Prior Publication Data
US 2013/0122467 A1    May 16, 2013

Related U.S. Application Data

(63) Continuation of application No. 12/771,105, filed on Apr. 30, 2010, now abandoned.

(51) Int. Cl.
| *A61K 6/00* | (2006.01) |
| *A61N 5/06* | (2006.01) |
| *A61K 8/22* | (2006.01) |
| *A61K 8/36* | (2006.01) |
| *A61K 8/49* | (2006.01) |
| *A61Q 11/00* | (2006.01) |

(52) U.S. Cl.
CPC .............. *A61K 6/0061* (2013.01); *A61K 8/22* (2013.01); *A61K 8/36* (2013.01); *A61K 8/498* (2013.01); *A61N 5/062* (2013.01); *A61Q 11/00* (2013.01); *A61K 2800/434* (2013.01); *A61K 2800/592* (2013.01)

(58) Field of Classification Search
USPC .......... 424/78.37, 443, 486; 423/579; 522/13, 522/84
See application file for complete search history.

(56) References Cited

U.S. PATENT DOCUMENTS

| 2,877,221 | A | | 3/1959 | Lanbach |
| 3,293,127 | A | | 12/1966 | Beck |
| 3,309,274 | A | * | 3/1967 | Brilliant ................ A61B 10/00 106/35 |
| 3,372,125 | A | | 3/1968 | Hill |
| 3,595,798 | A | | 7/1971 | Smith et al. |
| 3,652,420 | A | | 3/1972 | Hill |
| 3,728,446 | A | | 4/1973 | Roberts et al. |
| 4,574,097 | A | | 3/1986 | Honeycutt |
| 4,846,165 | A | | 7/1989 | Hare et al. |
| 4,891,211 | A | | 1/1990 | Winston |
| 4,992,256 | A | | 2/1991 | Skaggs et al. |
| 5,658,148 | A | | 8/1997 | Neuberger et al. |
| 5,749,968 | A | | 5/1998 | Melanson et al. |
| 5,785,527 | A | | 7/1998 | Jensen et al. |
| 5,844,016 | A | * | 12/1998 | Sawhney et al. ................ 522/13 |
| 5,858,332 | A | | 1/1999 | Jensen et al. |
| 5,922,331 | A | | 7/1999 | Mausner |
| 5,977,199 | A | | 11/1999 | Xie |
| 6,030,222 | A | | 2/2000 | Tarver |
| 6,036,493 | A | | 3/2000 | Sharma |
| 6,056,548 | A | | 5/2000 | Neuberger et al. |
| 6,084,005 | A | | 7/2000 | Fukunishi et al. |
| 6,107,466 | A | | 8/2000 | Hasan et al. |
| 6,121,341 | A | | 9/2000 | Sawhney et al. |
| 6,149,895 | A | | 11/2000 | Kutsch |
| 6,162,055 | A | | 12/2000 | Montgomery et al. |
| 6,254,388 | B1 | | 7/2001 | Yarborough |
| 6,267,976 | B1 | | 7/2001 | Barnhart et al. |
| 6,337,357 | B1 | | 1/2002 | Fukunishi et al. |
| 6,343,933 | B1 | | 2/2002 | Montgomery et al. |
| 6,361,329 | B1 | | 3/2002 | Dekker et al. |
| 6,365,134 | B1 | | 4/2002 | Orlowski et al. |
| 6,387,353 | B1 | | 5/2002 | Jensen et al. |
| 6,391,283 | B1 | | 5/2002 | Jensen et al. |
| 6,420,455 | B1 | | 7/2002 | Landgrebe et al. |
| 6,423,697 | B1 | | 7/2002 | Friedman |
| 6,440,396 | B1 | | 8/2002 | McLaughlin |
| 6,444,725 | B1 | | 9/2002 | Trom et al. |

(Continued)

FOREIGN PATENT DOCUMENTS

| CA | 2 222 027 A1 | 6/1998 |
| CA | 2 551 613 | 12/2005 |

(Continued)

OTHER PUBLICATIONS

Berneburg et al., "Phototherapy with Narrowband UVB," Acta Derm Venereol, 85(1-11) (2005).
Sezer et al., "Topical Drug Delivery Using Chitosan Nano- and Microparticles," Informa UK, pp. 1129-1146, (ISSN 1742-5247 (2012).
Fischersci, :Material Safety Data Sheet: Sodium acetate buffer. https://fscimagef.fishersci.com/msds/91502.htm (Apr. 13, 2000).

(Continued)

*Primary Examiner* — Walter Webb
(74) *Attorney, Agent, or Firm* — Ropes & Gray LLP (57) ABSTRACT

Disclosed herein are compositions that can rapidly evolve oxygen and/or activated oxygen generally including an oxidizing agent (e.g., a peroxide) and an activating agent that has an emission wavelength between about 400 nm and about 570 nm (e.g., Eosin B, Eosin Y, or Erythrosine B). Methods of employing these compositions to whiten teeth, and methods of making these compositions and kits that include some or part of the composition ingredients, are also described.

11 Claims, 2 Drawing Sheets

(56) References Cited

U.S. PATENT DOCUMENTS

| | | |
|---|---|---|
| 6,475,497 B1 | 11/2002 | Rajaiah et al. |
| 6,485,709 B2 | 11/2002 | Banerjee et al. |
| 6,488,914 B2 | 12/2002 | Montgomery |
| 6,514,543 B2 | 2/2003 | Montgomery |
| 6,528,555 B1 | 3/2003 | Nikutowski et al. |
| 6,536,628 B2 | 3/2003 | Montgomery |
| 6,541,460 B2 | 4/2003 | Petito |
| 6,558,653 B2 | 5/2003 | Andersen et al. |
| 6,846,182 B1 | 1/2005 | Sibner |
| 6,905,672 B2 | 6/2005 | Rajaiah et al. |
| 6,960,079 B2 | 11/2005 | Brennan et al. |
| 7,114,953 B1 | 10/2006 | Wagner |
| 7,220,438 B2 | 5/2007 | Quintanilla Almagro et al. |
| 7,314,470 B2 | 1/2008 | Malodobry |
| 7,354,448 B2 | 4/2008 | Altshuler et al. |
| 8,075,875 B2 | 12/2011 | Piergallini et al. |
| 8,334,328 B2 | 12/2012 | Marmarinos et al. |
| 8,414,911 B2 | 4/2013 | Mattson |
| 8,632,822 B2 | 1/2014 | Piergallini et al. |
| 8,637,086 B2 | 1/2014 | Piergallini et al. |
| 8,658,219 B2 | 2/2014 | Piergallini et al. |
| 8,685,466 B2 | 4/2014 | Piergallini et al. |
| 8,911,791 B2 | 12/2014 | Piergallini et al. |
| 8,974,833 B2 | 3/2015 | Piergallini et al. |
| 8,986,719 B2 | 3/2015 | Piergallini et al. |
| 8,986,745 B2 | 3/2015 | Piergallini et al. |
| 8,986,746 B2 | 3/2015 | Piergallini et al. |
| 2001/0022970 A1 | 9/2001 | Dees et al. |
| 2003/0133940 A1 | 7/2003 | Dees et al. |
| 2003/0198605 A1 | 10/2003 | Montgomery |
| 2004/0026569 A1 | 2/2004 | Preston |
| 2004/0136971 A1 | 7/2004 | Scharp et al. |
| 2004/0191330 A1 | 9/2004 | Keefe et al. |
| 2005/0020696 A1 | 1/2005 | Montgomery et al. |
| 2005/0026298 A1 | 2/2005 | Bickett et al. |
| 2005/0049228 A1 | 3/2005 | Albrecht et al. |
| 2005/0059731 A1 | 3/2005 | Albrecht et al. |
| 2005/0123588 A1* | 6/2005 | Zhu et al. .................. 424/443 |
| 2006/0099155 A1 | 5/2006 | MacDonald et al. |
| 2006/0198796 A1 | 9/2006 | Giniger et al. |
| 2006/0287211 A1 | 12/2006 | Barbizan et al. |
| 2007/0092469 A1 | 4/2007 | Jacobs |
| 2007/0128132 A1 | 6/2007 | Piergallini et al. |
| 2007/0166369 A1 | 7/2007 | Neuberger et al. |
| 2007/0191249 A1* | 8/2007 | Lant .................. C11D 3/168 510/376 |
| 2007/0244195 A1 | 10/2007 | Burkhart et al. |
| 2008/0108681 A1 | 5/2008 | Scimeca et al. |
| 2008/0113037 A1 | 5/2008 | Green et al. |
| 2008/0206159 A1 | 8/2008 | Tamarkin et al. |
| 2008/0305101 A1 | 12/2008 | Ruoslahti et al. |
| 2009/0238778 A1 | 9/2009 | Mordas et al. |
| 2010/0266989 A1 | 10/2010 | Piergallini et al. |
| 2011/0027753 A1 | 2/2011 | Maurat et al. |
| 2011/0218482 A1 | 9/2011 | Piergallini et al. |
| 2011/0224599 A1 | 9/2011 | Piergallini et al. |
| 2012/0095455 A1 | 4/2012 | Rodmond et al. |
| 2012/0171641 A1 | 7/2012 | Piergallini et al. |
| 2013/0281913 A1 | 10/2013 | Piergallini et al. |
| 2014/0105832 A1 | 4/2014 | Loupis et al. |
| 2015/0065453 A1 | 3/2015 | Piergallini et al. |

FOREIGN PATENT DOCUMENTS

| | | |
|---|---|---|
| CA | 2 580 381 | 1/2006 |
| CA | 2 580 381 A1 | 1/2006 |
| CA | 2632187 | 5/2008 |
| CA | 2677468 | 11/2011 |
| CA | 2797867 | 11/2011 |
| CN | 101594904 | 12/2009 |
| EP | 0356868 | 3/1990 |
| EP | 0 380 157 B1 | 8/1990 |
| EP | 0 704 539 A2 | 4/1996 |
| EP | 1 235 543 A1 | 9/2002 |
| EP | 1 235 544 A1 | 9/2002 |
| EP | 1 749 532 A1 | 2/2007 |
| EP | 1 779 891 A1 | 5/2007 |
| EP | 1 951 184 | 8/2008 |
| EP | 2 338 465 | 6/2011 |
| JP | 01-279838 | 11/1989 |
| JP | 02-233612 | 9/1990 |
| JP | 03-169805 A | 7/1991 |
| JP | 10-182390 A | 7/1998 |
| JP | 10-330235 | 12/1998 |
| JP | 10-330235 A | 12/1998 |
| JP | 2000-053550 | 2/2000 |
| JP | 2001-511137 A | 8/2001 |
| JP | 2002-502864 A | 1/2002 |
| JP | 2002-226349 A | 8/2002 |
| JP | 2002-293747 A | 10/2002 |
| JP | 2003-339875 A | 12/2003 |
| JP | 04-219756 B2 | 2/2009 |
| SG | 194945 | 11/2012 |
| WO | WO-81/00513 A1 | 3/1981 |
| WO | WO-90/09779 A1 | 9/1990 |
| WO | WO-91/02530 | 7/1991 |
| WO | WO-97/21420 | 6/1997 |
| WO | WO-98/10738 | 3/1998 |
| WO | WO-98/11827 | 3/1998 |
| WO | WO-98/23219 | 6/1998 |
| WO | WO-98/30169 | 7/1998 |
| WO | WO-98/33761 A1 | 8/1998 |
| WO | WO-9836700 | 8/1998 |
| WO | WO-99/04870 A1 | 2/1999 |
| WO | WO-99/39238 A1 | 8/1999 |
| WO | WO-99/40870 | 8/1999 |
| WO | WO-99/49823 A1 | 10/1999 |
| WO | WO-99/63900 | 12/1999 |
| WO | WO-01/00190 A2 | 1/2001 |
| WO | WO-01/12181 A1 | 2/2001 |
| WO | WO-02/22097 | 3/2002 |
| WO | WO-02087642 | 11/2002 |
| WO | WO-03/00215 A1 | 1/2003 |
| WO | WO-03/017824 A2 | 3/2003 |
| WO | WO-03/061696 A2 | 7/2003 |
| WO | WO-03/099247 A1 | 12/2003 |
| WO | WO-2004/028498 | 4/2004 |
| WO | WO-2004/081222 A2 | 9/2004 |
| WO | WO-2004073540 | 9/2004 |
| WO | WO-2005/009604 A1 | 2/2005 |
| WO | WO-2005/051305 A2 | 6/2005 |
| WO | WO-2006/014597 A1 | 2/2006 |
| WO | WO-2006/032847 | 3/2006 |
| WO | WO-2006/047868 A1 | 5/2006 |
| WO | WO-2006/072243 A1 | 7/2006 |
| WO | WO-2006/125650 A1 | 11/2006 |
| WO | WO-2006/135344 A1 | 12/2006 |
| WO | WO-2007025244 A2 | 3/2007 |
| WO | WO-2007/080453 A2 | 7/2007 |
| WO | WO-2008/011707 A1 | 1/2008 |
| WO | WO-2008/013962 A2 | 1/2008 |
| WO | WO-2008052081 | 5/2008 |
| WO | WO-2008096182 | 8/2008 |
| WO | WO-2009/089346 A2 | 7/2009 |
| WO | WO-2009089345 | 7/2009 |
| WO | WO-2010/051636 A1 | 5/2010 |
| WO | WO-2010/051641 A1 | 5/2010 |
| WO | WO-2011/006263 A1 | 1/2011 |
| WO | WO-2011/058448 A2 | 5/2011 |
| WO | WO-2011/134087 A1 | 11/2011 |
| WO | WO-2012126120 | 9/2012 |
| WO | WO-2013/155620 A1 | 10/2013 |
| WO | WO-2014040177 | 3/2014 |
| WO | WO-2014042936 | 3/2014 |

OTHER PUBLICATIONS

International Search Report (PCT/CA2013/000786) dated Jan. 8, 2014.

"Resources: Fluorochrome Absorption Emission Wavelengths" [Online] XP002449595 Retrieved from the Internet: URL: <http://www.scienceqateway.org/resource>s/fae1.htm>[retrieved on Sep. 6, 2007] see p. 2: Rhodamine WT emission nm 555 p. 2.

(56) References Cited

OTHER PUBLICATIONS

Alster et al., "Photodynamic therapy: practical cosmetic applications," Journal of Drugs in Dermatology, vol. 5(8); pp. 764-768, XP008147410 (2006).
Colman and Roenigk, "The healing of wounds in the skin of piglets treated with benzoyl peroxide," The Journal of Dermatologic Surgery and Oncology, XP 009151883, vol. 4(9), pp. 705-707 (1978).
FDA, Product Classification Database Search, Device: Eosin y: database updated Jun. 6, 2008.
Goldberg, David J., "Photodynamic therapy in skin rejuvenation," Clinics in Dermatology, vol. 26(6), pp. 608-613, XP025545890 (2008).
Kelly et al., "Combined photodynamic and photothermal induced injury enhances damage to in vivo model blood vessels," Lasers in Surgery and Medicine, vol. 34(5); pp. 407-413, XP008147412 (2004).
McCullach, et al., "Photosensitized destruction of Chlorella vulgaris by methylene blue or nuclear fast red combined with hydrogen peroxide under visible light irradiation," Environ. Sci. Tech, vol. 40, pp. 2421-2425 (2006).
Meisel, et al., "Photodynamic therapy for periodontal diseases: State of the art," Journal of Photochemistry and Photobiology B: Biology, 2005, 79, 159-170.
Publication date of following document established by Internet Archive Wayback Machine<URL: <http://web.archive.org/web/20090208211504/http://en.wikipedia.org/wiki/Eosin Aug. 2, 2009.
Rodgers, William, "Fluorescence Polarization Standards for High-Throughput Screening and Imaging," Bio Techniques, vol. 32, pp. 34-42 (2002).
Roy et al., "Dermal Wound Healing Is Subject to Redox Control," Molecular Therapy, vol. 13(1), XP005197711, pp. 211-220 (2006).
Sun, Grace, "Lasers and Light Amplification in Dentistry," retrieved online at http://www.sundds.comllaser/ on Jun. 23, 2005.
Antunes et al., "Evaluation of the clastogenicity and anticlastongenicity of the carotenoid bixin in human lymphocyte cultures," Mutat Res. 585(1-2):113-9 (2005).
Darzynkiewicz e al., "Photosensitizing effects of the tricyclic heteroaromatic cationic dyes pyronin Y and toluidine blue O (tolonium chloride)," Cancer Res., 48(5) 1295-9 (1988).
De et al., "Environmental effects on the aggregation of some xanthene dyes used in lasers," Spectrochim Acta A Mol Biomol Spectrosc., 61(8) 1821-33 (2005).
Jankowski et al., "The action of photosensitizers and serum in a bactericidal process. II. The effects of dyes: hypericin, eosin Y and saphranine O," Pol J Microbiol., 54(4):323-30 (2005).
Montenegro et al., "Model studies on the photosensitized isomerication of bixin," J Agric Food Chem, 52(2): 367-73 (2004).
Nolan et al., "The efficacy of topical hyaluronic acid in the management of oral lichen planus," Journal of Oral Pathology and Medicine, 38:3, pp. 299-303 (Feb. 23, 2009), XP055103025.
Steinberg et al., "Genetic and Physiological Effects of Noncoherent Visible Light Combined with Hydrogen Peroxide on *Streptococcus mutans* in Biofilm," Antimicrobial Agents and Chemotherapy, 52:7, pp. 2626-2631, (Mar. 3, 2008) (XP055103315).
Subba et al, "Photocatalytic transformation of dyes and by-products in the presence of hydrogen peroxide," Environ Technol., 24(8) 1025-30 (2003).
Ariizumi et al., "Clinical Evaluation of a Topical Applicant TSG-88 for Periodontal Disease," Dental Drug Therapy, 10(2):157-168 (1998) (English Abstract included).
Eurasian Search Report, Serial No. 201291068, dated May 29, 2013 with English translation (3 pages).
European Search Report and Written Opinion, Application No. EP11161795, dated May 23, 2011.
PCT International Search Report and Written Opinion for International Serial No. PCT/CA2011/050261, dated Aug. 4, 2011 (6 pages).
PCT International Search Report and Written Opinion for International Serial No. PCT/CA2012/050177, dated Jun. 28, 2012 (8 pages).
PCT International Search Report and Written Opinion for International Serial No. PCT/GR2007/000006, dated Oct. 12, 2007 (8 pages).
PCT International Search Report and Written Opinion for International Serial No. PCT/IB2006/004034, dated Sep. 20, 2007 (13 pages).
Chen et al., "Study of the chemiluminescent characteristics of some xanthone dyes," Analytica Chimica Acta, 292(1-2):159-167 (1994).
Mintel, "Teens Braces Cleaner," http://gnpd.com, Jan. 2004 (2 pages).

* cited by examiner

FIG 1
Effect of Light Emitting Diode (LED) exposure on the compositions

FIG 2

Photoactive booster with different colors 5 h after extrusion from a syringe

# PHOTOACTIVATABLE OXYGEN-EVOLVING COMPOSITIONS AND METHODS FOR TEETH WHITENING

CROSS-REFERENCE TO RELATED APPLICATIONS

This application is a national stage filing under 35 U.S.C. §371 of International Application No. PCT/CA2011/050261, filed on Apr. 29, 2011, which claims priority to and is a continuation of U.S. patent application Ser. No. 12/771,105, filed Apr. 30, 2010, the contents of which are hereby incorporated by reference. International Application No. PCT/CA2011/050261 was published under PCT Article 21(2) in English.

FIELD OF THE INVENTION

The present invention relates generally to compositions that evolve oxygen and/or activated oxygen, which are useful in applications such as teeth whitening. More specifically, the invention relates to teeth whitening compositions and kits that can be employed to provide a desired whitening effect (e.g., at least two shades of whitening) in less than about 5 minutes of total exposure to actinic light without significant post-treatment sensitivity.

BACKGROUND OF THE INVENTION

Peroxide and peroxyacid compounds, such as hydrogen peroxide and carbamide peroxide, have been disclosed as useful in teeth whitening compositions. Application of UV or visible light from, e.g., Argon lasers, has been employed to accelerate whitening after application of peroxide compositions to the teeth. Additionally, whitening compositions have been described that include compounds capable of absorbing light and converting it to heat or chemical energy, such as the metal-ligand complexes and metal chelate precursors described in U.S. Pat. No. 6,343,933 to Montgomery et al.

Red dyes have also been employed to absorb visible or UV energy and produce heat in a bleaching composition as described, e.g., in U.S. Pat. No. 6,485,709 to Banerjee et al. This patent also describes attempts to further enhance such compositions by adding metal ions, or an organo-metallic enzyme (e.g., catalase), or by using high pH (e.g., above 7) to destabilize or activate the decomposition of hydrogen peroxide. Teeth whitening compositions have also been described that include violet or blue-violet dyes to counter-stain yellow teeth in U.S. Pat. No. 6,030,222 to Tarver. Rhodamine B dye has been employed in a teeth whitening composition as described in WO 02/22097 to Verheyen et Tooth sensitivity following treatment, and the time required for teeth whitening compositions (typically requiring about an hour of time or multiple applications or both), however, remains a significant drawback.

SUMMARY OF THE INVENTION

The present invention provides novel compositions and methods that that evolve oxygen and/or activated oxygen and are capable of, for example, whitening teeth in a surprisingly short amount of time (e.g., less than 1 minute to about 10 minutes) and with minimal or no sensitivity post-treatment. The invention is based, in part, on the discovery that the use of the dyes described herein dramatically accelerates the whitening process.

Without wishing to be bound to any particular theory, it is believed that inclusion of these dyes significantly enhances the compositions of the invention at least because it is believed that dentin transmits green light and absorbs blue light. Accordingly, the dyes of the present invention enhance whitening not only at the surface of the tooth, but also may be transmitting light into the tooth to enhance the alteration of color agents by radicals that have penetrated into the tooth surface.

Another advantage of the present invention is that the compositions can be effective when applied only for a short period of time (e.g., 1 minute in some embodiments). Accordingly, sensitivity due to, e.g., percolation of hydrogen peroxide to the pulp tissue (e.g., pulpal inflammation), may be minimized or eliminated. Another advantage of the present invention is that the compositions do not require compounds that generate heat, and therefore, discomfort associated with compositions that generate heat may be minimized or eliminated. Yet another advantage is that dyes can be used (e.g., Eosin) that are less toxic than dyes such as Rhodamine B.

In one aspect, the present invention features a tooth whitening composition which includes an oxidizing agent and an activating agent having an emission wavelength between about 400 nm and about 570 nm.

In one embodiment, the activating agent is capable of emitting green light, blue light or blue-green light, and/or absorbs green light, blue light or blue-green light. In another embodiment, the activating agent comprises Eosin (e.g., eosin Y, eosin B), Erythrosine, or both.

In another embodiment, the composition further includes a stabilizing agent. In one embodiment, the stabilizing agent is sodium acetate.

In one embodiment, the composition further includes a thickening agent.

In one embodiment, the thickening agent is silicon dioxide and/or fumed silica having a particle size less than one micron.

In one embodiment, the composition further includes a hydrophilic gelling agent.

In another embodiment, the composition further includes an accelerator agent. In some embodiments, the accelerator agent includes sodium perborate.

In one embodiment, the pH of the composition is between about 8 and about 10.

The invention also features a method for tooth whitening including applying the tooth whitening composition of the present invention to at least one tooth, and exposing the tooth whitening composition to actinic light such that the tooth is whitened at least about one shade. In one embodiment, the tooth is whitened at least about two shades in less than about 10 minutes or in less than about 5 minutes.

In one embodiment, post-treatment sensitivity is insignificant or eliminated.

In one embodiment, the tooth is exposed to the tooth whitening composition for less than 5 seconds per application.

The invention also features a kit for tooth whitening including a tooth whitening composition of the invention and an apparatus for preparing and/or applying the composition.

The invention also features a kit for tooth whitening including a tooth whitening composition of the invention and instructions for determining a composition application time to achieve a desired whitening effect.

The invention also features a method for tooth whitening including at least one application of actinic light and a tooth whitening composition to at least one tooth such that the tooth is whitened at least about two shades with less than about 1 minute of total exposure to actinic light. In one embodiment, the tooth is whitened at least about three shades in less than about 30 seconds. In another embodiment, there is no significant post-treatment sensitivity.

DETAILED DESCRIPTION OF THE PREFERRED EMBODIMENTS

In order to more clearly and concisely describe the subject matter of the claims, the following definitions are intended to provide guidance as to the meaning of specific terms used in the following written description, examples and appended claims.

The term "accelerating agent" refers to any agent capable of accelerating and/or contributing to the completion of radical generation (e.g., sodium perborate).

The term "actinic light" refers to light energy capable of being absorbed by an activating agent.

The term "activating agent" refers to any agent capable of absorbing actinic light. Preferably, the activating agent enhances and/or accelerates the dispersion of light energy, or otherwise enhances and/or activates the decomposition of an oxidizing agent. Activating agents include agents capable of absorbing light energy and emitting light energy, e.g., fluorochromes. Suitable activating agents include e.g., Eosin, which refers to Eosin B, Eosin Y, or a combination thereof, and Erythrosine B (also known as Erythrosine).

The term "eosin" refers to fluorescent red dye resulting from the action of bromine on fluorescein. There are two very closely related compounds commonly referred to as eosin. Eosin Y is a tetrabromo derivative of fluorescein (also known as eosin Y ws, eosin yellowish, Acid Red 87, C.I. 45380, bromoeosine, bromofluoresceic acid, D&C Red No. 22); it has a very slightly yellowish cast. The other eosin compound, eosin B, is a dibromo derivative of fluorescein (eosin bluish, Acid Red 91, C.I. 45400, Saffrosine, Eosin Scarlet, or imperial red); it has a very faint bluish cast.

The term "erythrosine" refers to fluorescent cherry-pink fluorone food coloring. It is the disodium salt of 2,4,5,7-tetraiodofluorescein. It is also known as FD&C Red No. 3, Food Red 14, and Acid Red 51. Erythrosine is also known as erythrosine B.

The term "oxidizing agent" refers to any agent capable of oxidizing, and also includes precursors of compounds capable of oxidizing. Examples of oxidizing agents include, but are not limited to, peroxide, peroxy acid, hydrogen peroxide, carbamide peroxide, alkali metal peroxides, alkali metal percarbonates, peroxyacetic acid, and alkali metal perborates.

The term "post-treatment sensitivity" refers to sensitivity or instant pain experienced by a subject after a tooth whitening procedure. Sensitivity can include, but is not limited to, stimuli such as temperature and pressure. Instant pain typically occurs without stimuli. The terms "significant sensitivity" or "significant post-treatment sensitivity" and the like, refer to significant discomfort post-treatment, including sensitivity and/or instant pain for more than four hours. The term "insignificant pain" refers to minimum sensitivity to stimuli such as temperature and/or pressure for less than four hours post-treatment.

The term "stabilizing agent" refers to any agent that stabilizes one or more agents of the composition (e.g., an oxidizing agent such as hydrogen peroxide). The stabilizing agent can act to stabilize the agent or agents against spontaneous or unwanted reactivity in use and/or in storage. Suitable stabilizing agents include sodium acetate. In some instances, the stabilizing agent can stabilize hydrogen peroxide for about one year.

The term "total exposure to actinic light" refers to the total time a tooth is exposed to actinic light including multiple applications of actinic light over the course of a treatment session.

The term "transparent" refers to a composition capable of at least 70% transmission of light. The term "translucent" refers to a composition capable of at least about 40% transmission of light. The light referred to can be, e.g., actinic light (e.g., from a laser), emitted light (e.g., from a fluorochrome), or both.

The term "translucency agent" refers to any agent capable of increasing the translucency of a composition. Such agents can increase translucency, e.g., upon addition to the composition, upon activation (e.g., by heat, actinic light and/or emitted light), or both.

When ranges are disclosed herein (e.g., wavelength, pH, concentration, particle sizes, and whitening ranges) all individual values and ranges within the disclosed ranges are regarded as part of and encompassed by the present invention. All concentrations are provided in weight % of the composition unless indicated otherwise.

Where "a", "an" or the like is used herein, these articles are used in the open or non-restrictive sense, e.g., to indicate "at least one" or "one or more". Similarly, the term "or" is used in the open or nonrestrictive sense, i.e., to mean "and/or." Accordingly, the terms "or" and "and/or" are used interchangeably and are meant to have the same meaning.

In one aspect, the present invention provides tooth whitening compositions that include an oxidizing agent (e.g., hydrogen peroxide), and an activating agent that has an emission wavelength between about 400 nm and about 570 nm (e.g., Eosin B, Eosin Y, Erythrosine B or combinations thereof). The composition can also include additional agents including, but not limited to, pH adjusting agents, thickening agents, stabilizing agents, accelerating agents, gelling agents, translucency agents.

The oxidizing agent can be any oxidizing agent known in the art. In one embodiment, the oxidizing agent includes hydrogen peroxide or sodium perborate or both. Additionally or alternatively, the oxidizing agent can include carbamide peroxide, alkali metal peroxides, alkali metal percarbonates, alkali metal perborates or combinations of these compounds. The oxidizing agents can be, e.g., liquid, gel, or paste compositions capable of interacting with the activating compound when exposed to actinic light.

The concentration of the oxidizing agent can be varied in the present invention. In one embodiment, the oxidizing composition includes a hydrogen peroxide, e.g., in a range of about 1% to about 70%. In a further embodiment, the oxidizing composition includes about 50% hydrogen peroxide.

The activating agent can include any agent with an emission wavelength between about 400 nm and about 570 nm. In another embodiment, the activating agent emits light in the range of between about 435 nm and about 520 nm. In one embodiment, the activating agent emits light in the range of between about 520 nm and about 565 nm. In certain embodiments, the agent both absorbs and emits light in the above ranges. In one embodiment, the activating agent emits green light. In another embodiment, the activating agent emits blue-green light. In one embodiment the activating agent both absorbs and emits green light.

In one embodiment, the activating agent includes at least one of Eosin B, Eosin Y, or Erythrosine B or combinations thereof In another embodiment, the whitening composition includes in the range of about 0.5% to about 0.8%, or between about 0.02% and about 1.2% or less than about 12% of at least one of Eosin B or Eosin Y or combinations thereof, or from about 0.02% to about 12% (e.g., 0.02-0.5%, 0.02-0.2%, 0.05-0.15%, 0.05-0.1%) of at least one of Eosin B or Eosin Y or combinations thereof In yet another embodiment, the composition includes about 0.02% to about 12% of Eosin B or Eosin Y or combinations thereof, and/or from about 0.01% to about 1%, or about 0.005% and about 0.15%, or from about 0.005% to 1% of Erythrosine B. It is believed that the combination of Eosin B and/or Eosin Y and/or Erythrosine B has a synergistic effect. It is believed this synergistic effect may be related to the close absorption peaks of the dyes. It is further believed that because Eosin B and/or Eosin Y and Erythrosine B reemit green light, that this green light can and may be further absorbed (or reabsorbed) by the fluorochromes so that light energy is not dissipated as in conventional compositions. This absorbed and re-emitted light not only penetrates throughout the bleaching gel, but also is transmitted into the enamel and dentin. Dyes such as Eosin B and Eosin Y are also advantageous as they are significantly less toxic than dyes such as Rhodamine B.

Without wishing to be bound to any particular theory, it is believed that because dentin and enamel transmit green light, light in this range can be transmitted into the dentin and/or enamel of the tooth, causing excitation of electrons in specific chemical bonds within the activating agent and tooth chromophores, making them more susceptible to be attacked by free radicals. The activating agents of the invention can include blue-green and/or blue emitting dyes. Accordingly, the present invention is based, at least in part, on the discovery that the use of the activating agents of the invention significantly enhance and/or contribute to the enhancement of a whitening effect in a fraction of the time required by conventional compositions. Because the teeth are only exposed to the whitening composition for a fraction of the time as compared to conventional teeth whitening compositions, superficial cracks and crevices, caused by prolonged exposure to free radicals, can be reduced or eliminated. Because decalcification can occur in the cracks and crevices caused by prolonged exposure to free radicals, stains more easily return as the decalcified enamel acts as a sponge. In the present invention, the decreased exposure time to free radicals reduces the possibility of crevices and cracks, thus leading to a significantly prolonged or permanent whitening effect for deeper pigments. Moreover, prolonged periods of exposure cause the enamel to become brittle. It is believed that the composition and methods of the present invention avoid compromise of the enamel.

In one embodiment, the activating agent or agents not only are capable of emitting light in the wavelength range from about 400 nm to about 570 nm, but also absorb light in the wavelength range from about 400 nm to about 570 nm. Such an activating agent is activated by light in the wavelength range of from about 400 nm to about 570 nm. Accordingly, in one embodiment the activating agent absorbs light in the wavelength range of about 400 nm to about 570 nm. In another embodiment, the activating agent absorbs light at a wavelength between about 470 nm to about 550 nm. This embodiment therefore allows for the optimal absorption of energy from the actinic light and the optimal transmission through dentin and enamel.

Without wishing to be bound to any particular theory, it is also believed that activating agents of the present invention, when exposed to actinic light, can accelerate the dispersion of light energy which consequently leads to an instantaneous and complete photochemical activation of the peroxide within the gel. It is believed that the gel mass better transmits light in the wavelength range of about 400 nm to about 570 nm, so that when an activating agent is exposed to actinic light, the dispersion of the light energy leads to an accelerated photochemical activation of the peroxide. Together, these embodiments allow for optimal absorption by the activating agent of energy from the actinic light and the optimal transmission through the composition, dentin and enamel.

In one embodiment, the composition also includes a stabilizing agent. In one embodiment, the stabilizing agent stabilizes the peroxide concentration in the composition for days, weeks, months, a year or several years. In one embodiment, the stabilizing agent not only stabilizes the oxidizing agent, but also is a pH modifier and/or stabilizer. In another embodiment, the stabilizing agent is sodium acetate. In one embodiment, sodium acetate is added until the desired pH is attained. In yet another embodiment, the composition includes between about 0.1% and about 50% stabilizing agent. Any value or range within this range is meant to be encompassed.

In one embodiment, the stabilizing agent is selected from the group consisting of antioxidants such as sodium sulfite, metal chelators (e.g., EDTA), and stabilizers (e.g., tin salts, phosphoric acid, and tin sulphonates). In some embodiments, the stabilizing agent scavenges or otherwise isolates or removes from solution, metal ions that can potentially destabilize the hydrogen peroxide.

In one embodiment, the stabilizing agent is or includes sodium acetate (e.g., sodium acetate trihydrate). Sodium acetate has been found to inhibit spontaneous reactivity of hydrogen peroxide and therefore can provide improved stability.

In one embodiment, the pH of the composition is in or adjusted to the range of from about 4 to about 10. In alkaline conditions, with a pH from about 8 to about 10, the stronger free radical, perhydroxyl ions, can be generated. Perhydroxyl free radicals are capable of reacting not only with yellow and brown stains but even with grey chromophores situated deeper in the tooth structure. In further embodiments, the pH of the composition is between about 5 and about 7, or between about 5 and about 6. In certain embodiments the pH is about 6.

Suitable pH adjusting agents include, but are not limited to, sodium hydroxide, potassium hydroxide, ammonium hydroxide, sodium carbonate, potassium carbonate, TRIS, and triethanolamine, or any other salt of an alkaline base which is safely used in the mouth. In another embodiment, the pH adjusting agent is sodium perborate. In certain embodiments of the invention, a single component may act as a pH adjusting agent or as a stabilizing agent or may serve both functions. In one embodiment, sodium acetate acts as a pH adjusting agent and as a stabilizing agent. In further embodiments, the pH adjusting agent is of the group consisting of sodium bicarbonate, calcium bicarbonate, sodium carbonate and calcium carbonate.

Additionally or alternatively, the composition can include a thickening agent to improve the ease of application of the composition to the teeth such that even and effective coverage is more readily achieved. Suitable thickening agents include but are not limited to mixed silica-aluminum oxides, long chain hydrocarbons such as synthetic carbomers (e.g., Carbopol), triethanolamine (e.g., Trolamine), and water soluble poly (ethylene oxide) resins (e.g., Polyox™). Suitable thickening agents also include amide starches.

It has been found that using an agent which has a particle size in the range from about 0.2 microns (μm) to about 0.7 μm provides for more widespread dispersion of the oxidizing agent on the particle surface. Accordingly, in one embodiment, the activating agent has a particle size below about 2 microns or below about 1 micron. In other embodiments, the agent has a particle size below about 0.8, 0.7, 0.6, 0.5, 0.4, 0.3, or 0.2 microns. In other embodiments, the activating agent has a particle size between about 0.1 and about 0.8, between about 0.2 and about 0.7, or between about 0.3 and about 0.6 microns.

Additionally or alternatively, the thickening agent can include fumed silica and/or any other inert inorganic material that may be used as a carrier and can aid in the delivery of active oxygen to the tooth surface. Fumed silica of a small particle size (e.g., between about 0.2 microns and about 0.4 microns), can provide efficient dispersion of hydrogen peroxide and reflection of light energy within the oxidizing composition.

In some embodiments, the compositions of the invention include a reaction accelerator or accelerating agent. In one embodiment, the composition includes sodium perborate. Sodium perborate has selective reactivity with hydrogen peroxide in forming free radicals (reacts with water to release hydrogen peroxide). The use of one or more activating agents (e.g., sodium perborate) can be advantageous because they can absorb and retain heat generated in the composition by, e.g., actinic light, thus restricting any such heat to the gel in order to accelerate the reaction without heating the tooth, which can cause sensitivity. In addition, acceleration of the reaction means that the composition can be removed more quickly than conventional compositions thereby decreasing exposure of the patient to the composition and thus resulting in sensitivity and/or other damage to tissues and teeth.

In one embodiment, the compositions of the invention include between about 0.8% and about 15%, or between about 0.3% and about 18% of accelerator agent.

In further embodiments, the compositions of the invention include a gelling agent. Preferably the gelling agent is also a translucency agent. For example, a hydrophilic gelling agent can be employed to increase the translucency of the resulting composition or gel.

In some embodiments, the nature of the gelling agent (e.g., its hydrophilic nature) prevents vaporization of the gel when exposed to actinic light, thus improving hydration of the coated tooth area. Increased hydration of the teeth and surrounding tissues is associated with decreased discomfort and sensitivity. In one embodiment, the gelling agent can include, for example, one or more modified starches and/or glucose. In one embodiment, modified starches and/or glucose are activated in cold water. In some embodiments, the gelling agent further enhances the consistency of the composition, facilitating the application to the tooth surface.

The translucency agent can enhance translucency or transparency upon addition to the composition and/or upon activation by, e.g., actinic light, emitted light and/or heat. In one embodiment, it minimizes vaporization of the composition. Additionally or alternatively, the gelling and/or translucency agent minimizes any thermal effects by absorbing any heat generated in the composition.

In one embodiment the composition is a translucent composition. In another embodiment the composition is a transparent composition. In certain embodiments, the composition is translucent or transparent to the actinic light it will be exposed to (e.g., green, blue-green or blue light).

In one embodiment, the composition includes an oxidizing agent (e.g., hydrogen peroxide), an accelerating agent (e.g., sodium perborate), an activating agent (Eosin B, Eosin Y, Erythrosine B or combinations thereof), a stabilizing agent (e.g., sodium acetate trihydrate), a pH adjusting agent, a thickening agent (e.g., fumed silica or silicon dioxide or both), and a gelling agent. In one embodiment, the pH of the composition is from about 6 to about 10. In some embodiments, the pH of the composition is from about 8 to about 10. In other embodiments, the pH of the composition is from about 4 to about 10.

Another aspect of the invention provides a method for tooth whitening including applying a tooth whitening composition of the present invention to at least one tooth, and exposing the tooth whitening composition to actinic light to activate the oxidizing agent. The composition may be any of the compositions described herein.

In one embodiment, the method for bleaching the teeth is performed in a dentist's office or dental operatory under ordinary conditions. The composition can be mixed chair-side and applied to the surfaces of as many teeth as are desired to be whitened. Alternatively, the composition can be provided without the need for mixing chair-side. Thereafter, the composition can be exposed to actinic light to accelerate decomposition of the oxidizing agent and the formation of free radicals. In one embodiment, premixes can be prepared with some or all of the ingredients and then mixed chair-side and applied to the teeth. In one embodiment, a hydrogen peroxide/sodium acetate solution premix can be prepared and stored prior to use. Additionally or alternatively, some or all of the remaining ingredients can also be separately premixed and stored prior to use. Such premixes can be stored, e.g., for at least about one year.

The compositions of the invention can be used to whiten teeth discolored by any agent or disorder. For example, the compositions may be used to whiten discoloration due to stains (e.g., tobacco, coffee, tea and/or food stains), fluorosis, developmental disturbances, bacteria, genetics, tetracycline antibiotics, trauma, blood decomposition, pigments present during development of teeth, etc.

Any source of actinic light can be used and preferably it is capable of emitting light in a wavelength appropriate to the activating agent employed in the composition. In one embodiment, e.g., an argon laser is used. In another embodiment, a potassium-titanyl phosphate (KTP) laser (e.g., a GreenLight™ laser) is used as a light source. In one embodiment the light source emits light at or near the absorption wavelength of the activating agent or at least one of the activating agents, if several are included in the composition.

The most intense fluorescence (e.g., emission) from a fluorochrome dye occurs when it is irradiated with wavelengths close to the peak of the absorption wavelength (i.e., excitation curve). Accordingly, in one embodiment, the actinic light is at a wavelength of about the absorption wavelength of the activating agent. In one embodiment, the actinic light has a wavelength in the range from about 470 nm to about 550 nm. In another embodiment, the actinic light has a wavelength in the range from about 470 nm to about 520 nm. In yet another embodiment, an argon laser provides actinic light in the wavelength range from about 470 nm to about 520 nm. In a further embodiment, the actinic light has a wavelength of about 530 nm to about 535 nm. In still another embodiment, the source of actinic light is in the wavelength range of about 530 nm to about 535 nm is a KTP laser. In this embodiment the source is a KTP laser set at about 532 nm. In another embodiment, a photocuring device is the source of actinic light.

In one embodiment, the tooth is exposed to actinic light for less than 20 minutes, in another for less than 10 minutes, in another for less than 5 minutes. In one embodiment the tooth is exposed to actinic light for less than 4, 3, 2, or 1 minute. In one embodiment, the invention provides a method for whitening teeth at least 2 shades in about 1 minute. In some embodiments, there is no significant post-treatment sensitivity. In other embodiments, there is no post-treatment sensitivity.

In one embodiment, the tooth whitening composition is applied and the tooth is exposed to multiple applications of actinic light, for a time of about 4 to about 6 seconds each tooth per exposure. In some embodiments, the tooth is exposed to actinic light at least two, three, four, five or six times. In some embodiments, a fresh application of the tooth whitening composition is applied before each exposure to actinic light. In some embodiments, the total exposure to actinic light is less than about one minute. In other embodiments, the total exposure to actinic light is less than about 60, 40, 30, or 20 seconds.

In one embodiment, the tooth is whitened at least 7 shades, 6 shades, 5 shades, 4 shades, 3 shades, 2 shades or 1 shade. Shades can be determined before and after treatment using any of a number of shade guides, including, e.g., the VITA® (Vita Zahnfabrik H. Rauter GmbH & Co., KG), CHROMASCCP® (Ivoclar Vivadent, Inc.) or BIODENT (Dentsply International) shade guides. Optionally, a shade taking system, e.g., the ShadeEye NCC Dental Chroma Meter, can be employed to determine shade before and/or after treatment.

In one embodiment, the tooth is whitened at least two shades, three shades, four shades, five shades, six shades or seven shades in less than about one minute of total exposure time to actinic light. In some embodiments, the tooth is whitened at least two shades, three shades, four shades, five shades, six shades or seven shades in less than about 40 seconds of total exposure time to actinic light. In some embodiments, the tooth is whitened at least two shades, three shades, four shades, five shades, six shades or seven shades in less than about 30 seconds of total exposure time to actinic light. In some embodiments, the tooth is whitened at least two shades, three shades, four shades, five shades, six shades or seven shades in less than about 20 seconds or even less than about 10 seconds of total exposure time to actinic light.

In one embodiment, the risk of transient inflammation of the pulp by percolation of hydrogen peroxide is reduced, not significant and/or eliminated. Without wishing to be bound by any particular theory, inflammation of the pulp is thought to be caused by percolation of hydrogen peroxide into the pulp tissue. In some embodiments, the synergistic effect of the activating agents (e.g., Eosin B and/or Eosin Y and/or Erythrosine B) and the actinic light results in an instantaneous and complete photochemical reaction. Accordingly, exposure of the tooth, the pulp, and/or the surrounding tissues to the oxidizing agent and/or other components in the composition is dramatically reduced.

In yet another aspect, the invention provides a method for tooth whitening comprising application of actinic light and a composition of the invention (any of the compositions described herein) to at least one tooth such that the tooth is whitened at least about two shades in less than about 10 minutes. In another embodiment, the tooth is whitened at least about two shades in less than about 5 minutes, less than about 4 minutes, less than about 3 minutes, less than about 2 minutes or in about 1 minute. In some embodiments, the teeth are whitened at least about 3 shades, 4 shade or 5 shades. In some embodiments, there is no significant post-treatment sensitivity or no post-treatment sensitivity.

In yet another aspect, the invention provides a kit for preparing or applying a tooth whitening composition in accordance with the present invention. In one embodiment, the kit includes an oxidizing agent and an activating agent that has an emission wavelength between about 400 nm and about 570 nm. The composition can be any of the compositions of the present invention. In one embodiment, the composition is not combined, and may optionally include an apparatus to combine two or more components or premixes of the composition. In another embodiment the composition does not require any combination (i.e., it is ready to use and does not require any pre-mixing chair-side).

In another embodiment, the kit includes a composition of the invention and directions for application. Additionally or alternatively, the kit can include an apparatus for application (e.g., brushes or trays or both). The kit can also include charts or other information helpful in assessing the whitening effect desired and/or achieved by the methods and compositions of the invention. The kit can also include a source of actinic light.

Identification of equivalent compositions, methods and kits are well within the skill of the ordinary practitioner and would require no more than routine experimentation, in light of the teachings of the present disclosure. Practice of the invention will be still more fully understood from the following examples, which are presented herein for illustration only and should not be construed as limiting the invention in any way.

EXAMPLE 1

Preparation of an Exemplary Whitening Composition and Activation by Actinic Light A premix was prepared by mixing 4 mg of Eosin B, 1 mg of Erythrosine B, 450 mg of fumed silica, and 45 mg of sodium perborate. Separately, the pH of a 50% hydrogen peroxide solution was adjusted to pH 6 using sodium acetate solution. Approximately 4-6 ml of the adjusted hydrogen peroxide solution was then added to the premix in a plastic mixing chamber and immediately applied.

The gel was applied to frontal surface of the teeth of each subject beginning from the frontal anterior incisors, followed by the posteriors, and finally the posterior incisors. The gel was activated by a KTP laser set at a continuous wave of 0.5 watts. The laser was applied to each tooth for 2-3 seconds. During this time, the gel turned from orange-red to transparent and eventually became dull. After 3-4 minutes for two full arches from premolar to premolar, the gel was aspirated, and the teeth were lightly scrubbed with a cotton roll to clean the surface of the enamel. A second coating of gel was applied using fresh gel and activated with the KTP laser as described above. Up to six consecutive applications were performed to achieve the desired whitening effect for each patient. The duration of the sessions typically did not exceed 40 minutes.

EXAMPLE 2

Whitening Effect of Composition

A comparative study was conducted on 10 volunteers between an exemplary composition of the present invention and the SMARTBLEACH laser teeth whitening systems, which is a composition comprising Rhodamine B and hydrogen peroxide. The shade of each patient's teeth was recorded prior to application of whitening composition.

Teeth were coated with the composition prepared in Example 1 and exposed to actinic light from a green laser set at 532 nm for one minute for the entire mouth (4-5 seconds per tooth) and then the composition was removed. The comparative composition was applied to the teeth and exposed to light from a green laser set at 532 nm for 30 seconds per tooth and then left on the surface of the tooth for 10 minutes, in accordance with the manufacturer instructions provided with the composition. The comparative composition required at least 3 to 4 applications, for a total duration of about 1.5 hours for the entire mouth. The composition was removed from each volunteer and the teeth were irrigated with water. The teeth were then evaluated using the VITA scale for the whitening effect of the compositions. Patients were also evaluated for any post-treatment sensitivity by asking them to rate the level of pain experienced, if any.

The Smartbleach™ treatment resulted in a shade change of one to two shades in the yellow group, while the exemplary composition of the present invention resulted in a shade change of 5 shades in the yellow group, e.g., $A_4$ to $B_1$ VITA scale. In the "yellow group"($A_4$-$A_1$), treatment with the exemplary composition of the present invention resulted in shade changes of 4-5 shades, resulting in shades in the "white group" ($B_1$-$B_2$). Treatment with the exemplary composition for teeth in the "grey" ($C_4$-$C_1$) and "grey-brown" ($D_4$-$D_2$) groups showed changes of 2-3 shades in the first session.

The following evaluation scale of post-sensitivity was used:

| | |
|---|---|
| Level 0 | No sensitivity to thermal stimuli or any kind of pain following treatment. |
| Level 1 | Sensitivity to thermal stimuli that lasts for a few seconds. |
| Level 2 | Pain or discomfort that occurs due to thermal stimuli and lasts for more than one minute. Optional pain treatment with analgesics. |
| Level 3 | Pain or discomfort that occurs automatically, requiring use of analgesics to control the pain. |

Following treatment with the Smartbleach™ system, all ten subjects experienced pain from Level 1 to Level 3. Following treatment with the exemplary composition of the present invention, nine subjects experienced no pain (e.g., Level 0), and only one subject experienced pain of Level 1.

EXAMPLE 3

Effect of Actinic Light Source

A study was conducted on 28 volunteers comparing the effect of different actinic light sources in whitening with the composition of Example 1. A prophylactic session was performed on each patient 3-4 days before the bleaching session. The shade of each patient's teeth was recorded prior to application of whitening composition.

Teeth were coated with the composition prepared in Example 1 and exposed to different sources of actinic light: a green laser (KTP) at 532 nm, a blue-green (argon) laser at 480-514 nm, a photo curing halogen lamp, and a LED photocuring device. The activation was performed in the different patients for the left or the right sides of their dental arches according to an activation randomization mode. Specifically, a first patient's right side was activated with the 532 nm green laser, while the left side was activated with the 480 nm-514 nm blue-green laser. A second patient's right side was activated with the photocuring halogen lamp, while the left side was activated with the LED photo curing device. A third patient's right side was activated with the 532 nm green laser, while the left side was activated with the photocuring halogen lamp. A fourth patient's right side was activated with the 532 nm green laser, while the left side was activated with the LED photocuring device. A fifth patient's right side was activated with the 480 nm-514 nm blue-green laser, while the left side was activated with the photocuring halogen lamp. A sixth patient's right side was activated with the 480 nm-514 nm blue-green laser, while the left side was activated with the LED photocuring device.

The composition was removed from the teeth of each volunteer and the teeth were irrigated with water. The teeth were then evaluated using the VITA scale for the whitening effect of the compositions.

Activation by different photocuring devices produced comparable results. The speed of activation with the green laser and the blue-green laser was 4-5 seconds per tooth, while the speed of activation with the photo curing devices was about 10 seconds per tooth. Accordingly, a whitening session employing the green laser or the blue-green laser for the entire mouth would typically take approximately 30 minutes, and a session with a photocuring device would typically take approximately 40 minutes.

EXAMPLE 4

Preparation of Composition

Teeth whitening compositions were prepared according to the following table:

TABLE 1

| Description | Present Invention | Prior art |
|---|---|---|
| Activating agent | 1. Eosin Y (0.7 mg/g) <br> 2. Erythrosine B (0.7 mg/g) <br> 3. Eosin Y & Erythrosine B (both 0.7 mg/g) | 4. Acid Red 388 (0.7 mg/g) <br> 5. Acid Red 92 (0.7 mg/g) <br> 6. Acid Red 388 & Acid Red 92 (both 0.7 mg/g) <br> 7. FD&C Red 40 (0.7 mg/g) |
| Common components (Photoactive booster) | Hydrogen peroxide <br> Silica <br> Starch <br> Sodium perborate <br> Sodium Acetate <br> Distilled water | |

EXAMPLE 5

Clinical Assessment of Light Absorption and Quantitative Measurement of Fluorescence Emission Samples of each teeth whitening composition described in Table 1 were extruded from a syringe after mixing, and a portion of each extruded sample was exposed to actinic light for 60 seconds, while the remainder was not. Visual assessment of the change in color was performed and a photograph of the composition was taken immediately after light exposure.

Figure 1:
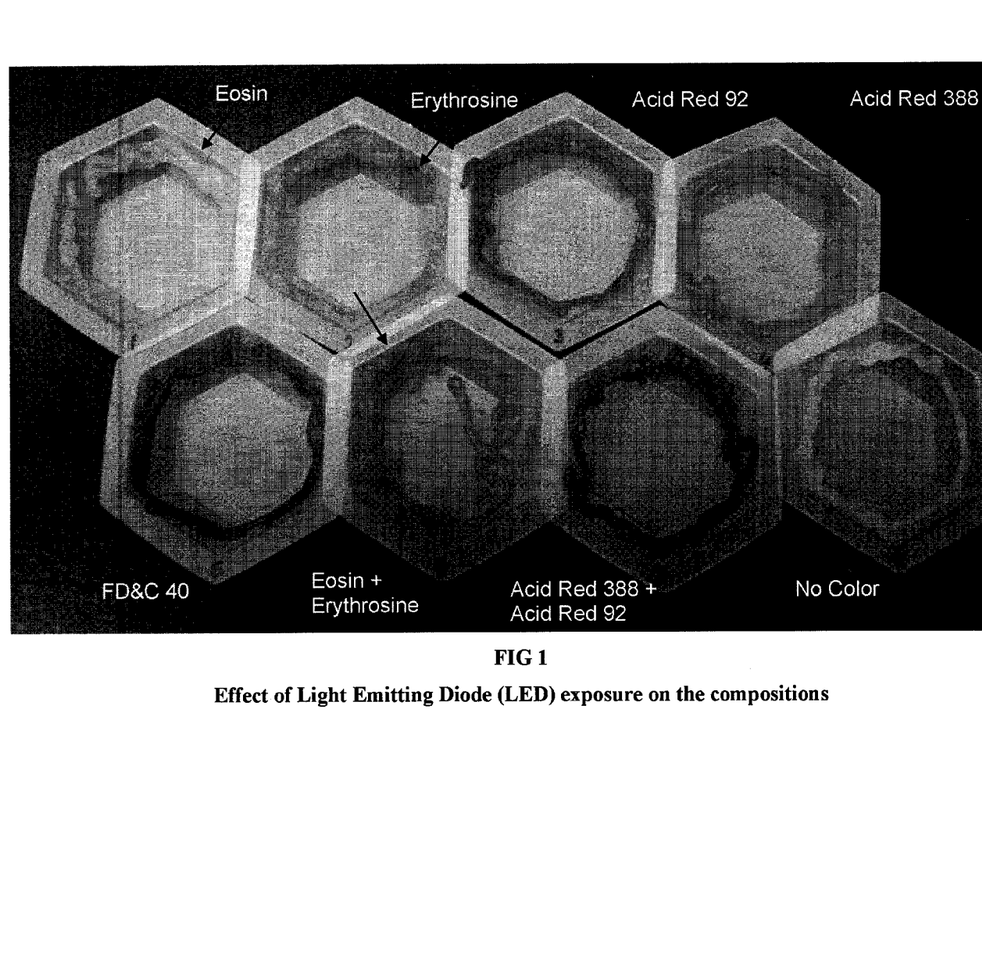
FIG. 1 illustrates compositions of the present invention compared to other compositions containing other dyes, before and after (see arrows) exposure to actinic light.

As shown in FIG. 1, prior to exposure to actinic light, all compositions displayed a clear and distinct coloring according to the dye used in the composition. During exposure to actinic light, the compositions of the present invention markedly fluoresced, as did the compositions containing the Acid Red dyes, but the composition containing FD&C Red 40 appeared non-fluorescent (results not shown). Following actinic light exposure, the coloring of the compositions of the present invention distinctly changed: the composition containing eosin Y alone turned a pristine white, while the composition containing erythrosine B and eosin Y+erythrosine B turned a bluish color. The compositions containing Acid Red 388 or Acid Red 92 alone, or a mixture of these two dyes did not change color. Lastly the compositions containing FD&C Red 40 was also unchanged. Thus, only the compositions of the present invention displayed any robust photochemical bleaching reactions.

Figure 2:
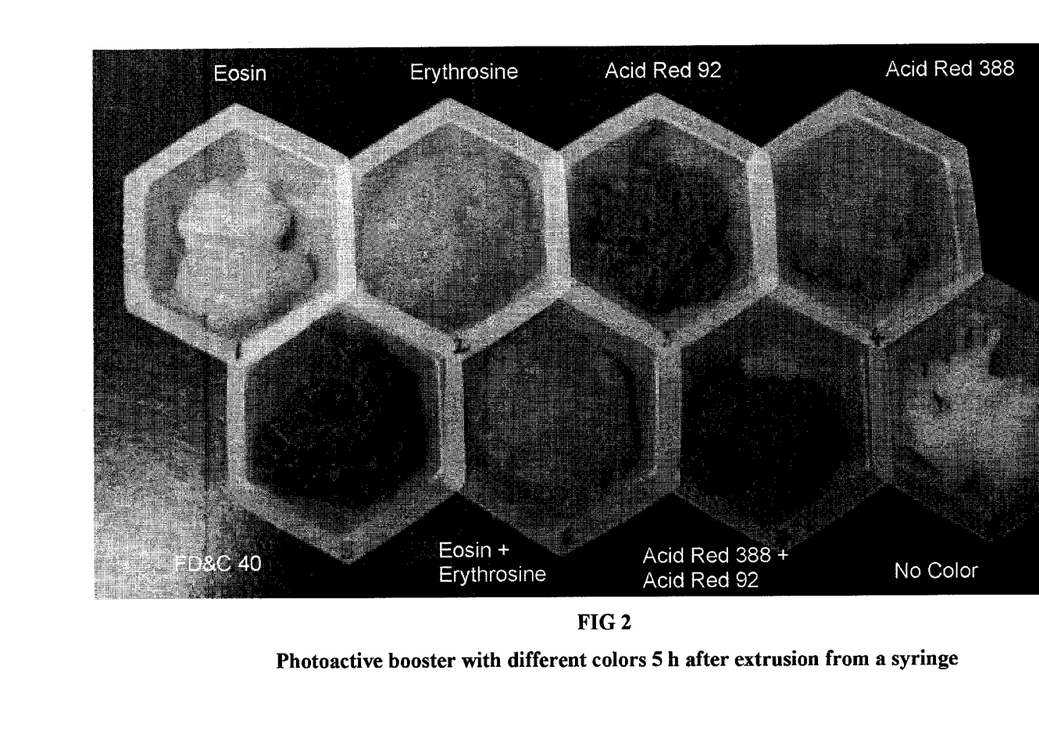
FIG. 2 illustrates compositions of the present invention compared to other compositions containing other dyes, after a 5 h period following extrusion of the compositions from a mixing syringe.

FIG. 2 shows that following actinic light exposure, all three of the compositions of the present invention became soft and moist, and collapsed into single mass of composition. The addition of sodium acetate to the gel composition accelerated the activation of the gel when exposed to actinic light. This acceleration may be caused by the increase in pH of the photoactive booster. Gas bubbles were observed emerging from the samples. This observation is consistent with a rapid and robust decomposition of hydrogen peroxide into water and oxygen (as per the known reaction: $2H_2O_2 \rightarrow 2H_2O+O_2$) accelerated by the dispersion of light energy in the composition by the activating agents. The other sample compositions did not mix into a single mass, but rather preserved a more solid texture, with strand-like aspects, as generated during extrusion from the syringe. As shown in FIG. 2, a second visual assessment was performed after the compositions had been left unattended for 5 hours at room temperature. Interestingly, the compositions of the present invention remained moist and showed evidence of gaseous releases, while the other compositions had hardened after this period. These results suggest that the compositions of the present invention are able to cause an accelerated photochemical activation of the hydrogen peroxide present in the composition. None of the other tested compositions displayed comparable results.

EXAMPLE 6

Teeth Whitening Results

Compositions containing eosin Y and erythrosine B, and compositions containing Acid Red 388 alone, Acid Red 92 alone and FD&C Red 40 alone were prepared as in Table 1 above. Each of the sample composition was directly and simultaneously tested on the teeth of a human subject. The mouth of each subject was divided in 4 quadrants (upper-left, lower-left, upper-right, and lower-right). To maintain a fixed optical position to assess teeth whitening, the composition of the present invention was in each case applied to the right quadrants, while the comparative composition was applied to the left quadrants. The compositions were exposed to actinic light (a Blue Phase LED photo curing device) for 20 seconds per tooth. The effect of each composition was scored according to the Vita® Brightness scale and results are shown in Table 2.

TABLE 2

Comparative results of teeth whitening using the composition of the present invention and compositions containing Acid Red dyes or FD&C Red 40

| Patient | Right quadrant | Vita shade conversion | Left quadrant | Vita shade conversion |
|---|---|---|---|---|
| 1 | Eosin Y and Erythrosine B | A3 to A1 (7 shades) | Acid Red 388 | A3 to A2.5 (>3 shades) |
| 2 | Eosin Y and Erythrosine B | A3 to A1 (7 shades) | Acid Red 92 | No change |
| 3 | Eosin Y and Erythrosine B | A3 to A1 (7 shades) | FD&C Red 40 | No change |

Vita ® Brightness scale B1 = lightest shade C4 = darkest shade

| B1 | A1 | B2 | D2 | A2 | C1 | C2 | D4 | A3 | D3 | B3 | A3,5 | B4 | C3 | A4 | C4 |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 |

For each of the three patients treated, use of the composition of the present invention resulted in a significant improvement of 7 shades (A3 to A1), while the composition containing Acid Red 388 caused a modest improvement slightly better than 3 shades (A3 to A2.5). Compositions containing Acid Red 92 or FD&C Red 40 had no effect whatsoever. Thus, the composition of the present invention is the most efficient teeth whitening composition.

The scientific results above show that based on exposure to actinic light, the red dyes used in the composition of the present invention are more readily activated. Also, these scientific results show that under the teeth whitening conditions of 20 seconds per teeth, use of Acid Red 388, Acid Red 92, or FD&C Red 40 do not result in a teeth whitening effect as potent as that of the composition of the present invention. In fact, Acid red 92 and FD&C Red 40 are unable to cause any teeth whitening effect under the conditions used. These results indicate that these dyes do not contribute as efficiently (if at all) as eosin Y or erythrosine B, to a teeth whitening effect.

EXAMPLE 7

Teeth Whitening Results

Compositions containing eosin Y alone, erythrosine B alone, both eosin Y and erythrosine B, and compositions containing Acid Red 388, Acid Red 92 alone or in combination, and FD&C Red 40 were prepared as Example 4 above. Each of the sample composition was directly tested on the teeth of a human subject. The compositions were exposed to actinic light (a Blue Phase LED photo curing device) for 20 seconds per tooth. The effect of each composition was scored according to the Vita Brightness scale and results are shown in Table 3.

TABLE 3

Comparative results of teeth whitening using the composition of the present invention and compositions containing Acid Red dyes or FD&C Red 40

| Patient | Dyes | Vita ® shade conversion |
|---|---|---|
| 1 | Eosin Y and erythrosine B | A3 to A1 (7 shades) |
| 2 | Eosin Y alone | A3 to A1 (7 shades) |
| 3 | Erythrosine B alone | A3 to C2 (2 shades) |
| 4 | Acid Red 388 | A3 to A2 (4 shades) |
| 5 | Acid Red 92 | No change |
| 6 | FD&C Red 40 | No change |
| 7 | Acid Red 388 and Acid Red 92 | A3 to A2 (4 shades) |

Vita ® Brightness scale B1 = lightest shade C4 = darkest shade

| B1 | A1 | B2 | D2 | A2 | C1 | C2 | D4 | A3 | D3 | B3 | A3,5 | B4 | C3 | A4 | C4 |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 |

For each of the three patients treated, use of the composition of the present invention containing eosin Y alone or eosin Y and erythrosine B resulted in a significant improvement of 7 shades (A3 to A1), while the composition containing Acid Red 388 alone or in combination with acid red 92 caused a modest improvement slightly better than 3 to 4 shades (A3 to A2.5 or A2). Compositions containing Acid Red 92 alone or FD&C Red 40 alone had no effect whatsoever. Thus, the composition of the present invention is the most efficient teeth whitening composition.

The scientific results above show that based on exposure to actinic light, the red dyes used in the composition of the present invention are more readily activated. Also, these scientific results show that under the teeth whitening conditions of 20 seconds per teeth, use of Acid Red 388, Acid Red 92, or FD&C Red 40 do not result in a teeth whitening effect as potent as that of the composition of the present invention. In fact, when used alone, Acid red 92 and FD&C Red 40 are unable to cause any teeth whitening effect under the conditions used. These results indicate that these dyes do not contribute as efficiently (if at all) as eosin Y or erythrosine B, to a teeth whitening effect.

The invention claimed is:

1. A composition comprising:
   about 1% to 70% of a peroxide; and
   about 0.02% to about 12% Eosin Y.

2. The composition according to claim 1, wherein the composition further comprises a thickening agent.

3. The composition according to claim 1, wherein the composition further comprises a hydrophilic gelling agent.

4. The composition according to claim 1, wherein the pH of the composition is between about 4 and about 10.

5. The composition according to claim 1, further comprising an accelerating agent.

6. The composition according to claim 3, wherein the accelerating agent is sodium perborate.

7. The composition according to claim 4, wherein the hydrophilic gelling agent is a modified starch.

8. The composition according to claim 2, wherein the thickening agent comprises a carbomer polymer.

9. The composition according to claim 1, wherein the composition is translucent or transparent.

10. The composition according to claim 1, wherein the peroxide is selected from hydrogen peroxide, carbamide peroxide, peroxy acid, peroxy acetic acid, sodium perborate, alkali metal peroxides, alkali metal percarbonates, alkali metal perborates, and combinations thereof.

11. The composition according to claim 1, wherein Eosin Y is present in an amount of about 0.05% to about 0.15%.

* * * * *

UNITED STATES PATENT AND TRADEMARK OFFICE
CERTIFICATE OF CORRECTION

PATENT NO. : 9,345,648 B2
APPLICATION NO. : 13/643672
DATED : May 24, 2016
INVENTOR(S) : Piergallini et al.

Page 1 of 1

It is certified that error appears in the above-identified patent and that said Letters Patent is hereby corrected as shown below:

In the Claims:

Claim 6, column 16, line 33, change "according to claim 3" to --according to claim 5--.

Signed and Sealed this
Nineteenth Day of July, 2016

Michelle K. Lee
*Director of the United States Patent and Trademark Office*